US005956126A

United States Patent [19]
Cody

[11] Patent Number: 5,956,126
[45] Date of Patent: Sep. 21, 1999

[54] OPTICAL INSTRUMENT AND METHOD FOR THE TREATMENT OF AMBLYOPIA

[76] Inventor: Victor Cody, 632 E. Olive, #B, Burbank, Calif. 91501

[21] Appl. No.: 08/972,264

[22] Filed: Nov. 18, 1997

Related U.S. Application Data

[60] Provisional application No. 60/031,361, Nov. 19, 1996.

[51] Int. Cl.$^{6}$ .................... A61B 3/00

[52] U.S. Cl. .................... 351/246; 351/203; 351/158

[58] Field of Search .................... 351/200, 203, 351/246, 158; 359/407, 411, 412, 418

[56] References Cited

U.S. PATENT DOCUMENTS

| | | | |
|---|---|---|---|
| 4,896,959 | 1/1990 | O'Brien | 351/203 |
| 5,374,820 | 12/1994 | Haaksman | 250/201.6 |
| 5,446,508 | 8/1995 | Kitchen | 351/169 |
| 5,450,144 | 9/1995 | Ben Nun | 351/219 |
| 5,452,026 | 9/1995 | Marcy, III | 351/45 |
| 5,465,737 | 11/1995 | Schachar | 128/898 |
| 5,483,301 | 1/1996 | Clarke | 351/158 |
| 5,503,165 | 4/1996 | Schachar | 128/898 |

*Primary Examiner*—Huy Mai
*Attorney, Agent, or Firm*—Merchant, Gould, Smith, Edell, Welter & Schmidt

[57] ABSTRACT

A method and apparatus for treating muscular disorders of the eye. The method comprising placing an object in front of the patient at a predetermined distance and placing a binocular optical system comprising lenses and prisms between the objects and the patient's eyes. A patch is placed over the patient's strong eye and the focal length of the optical system is adjusted so that the objects are clearly resolved by the patient. The patch is removed from the good eye so that the patient can repeat the exercise using both eyes. The object is then placed at a greater distance from the patient and the exercise is repeated until the resolution observed with the patient's weak eye is equal to the resolution observed with the patient's strong eye.

3 Claims, 1 Drawing Sheet

OPTICAL INSTRUMENT AND METHOD FOR THE TREATMENT OF AMBLYOPIA

CROSS REFERENCE TO RELATED APPLICATIONS

This application claims the benefit under 35 U.S.C. § 119(e) of U.S. Provisional Application Serial Number 60/031,361 filed Nov. 19, 1996 entitled "CORRECTION FOR A LAZY EYE" by Victor Cody, which application is also hereby incorporated by reference.

FIELD OF THE INVENTION

This invention relates to treatments to eye (vision) disorders and especially to treatment of a condition referred to as "lazy eye" in which the resolving power of one eye is less than the resolving power of another eye.

BACKGROUND OF THE INVENTION

The eyes of humans include a lens and a retina. When an observer views distant objects, each object is sufficiently small such that the object is perceived as a "point". In order for the eye to "see" either object, the curvature of the eye lens must be changed by the ciliary muscles so that an image of the object is focused on the retina. The signals from the retina tell the brain not only the distance between the objects, but also their position. However, the functioning of the brain is only as accurate as the signals it receives from the eyes. There are many conditions in which the eyes send inaccurate information as a result, in many cases, poor function of the eye muscles.

It is desirable to provide a means of correcting function by improving the muscle tone and function of the eye. It is also desirable that such a means is non-invasive.

SUMMARY OF THE INVENTION

The present invention is directed at a method and apparatus for treating muscular disorders of the eye. The method comprises placing an object in front of the patient at a predetermined distance and placing a binocular optical system comprising lenses and prisms between the objects and the patient's eyes. A patch is placed over the patient's strong eye and the focal length of the optical system is adjusted so that the objects are clearly resolved by the patient. The patch is removed from the good eye so that the patient can repeat the exercise using both eyes. The object is then placed at a greater distance from the patient and the exercise is repeated until the resolution observed with the patient's weak eye is equal to the resolution observed with the patient's strong eye.

The apparatus comprises a housing, eyepieces attached to a first side of the housing and two openings within the housing for receiving lenses and prisms such that the lenses and prisms are in alignment with the eye pieces. Means for adjusting the focal length of the lenses and prisms such that objects viewed by a patient through the eye pieces, lenses and prisms are clear and resolved and a cover for enclosing the openings are also provided.

BRIEF DESCRIPTION OF THE DRAWINGS

The present invention will be described with reference to the accompanying drawings, wherein like reference numerals identify corresponding or like components.

In the drawing.

DETAILED DESCRIPTION

Figure 1:
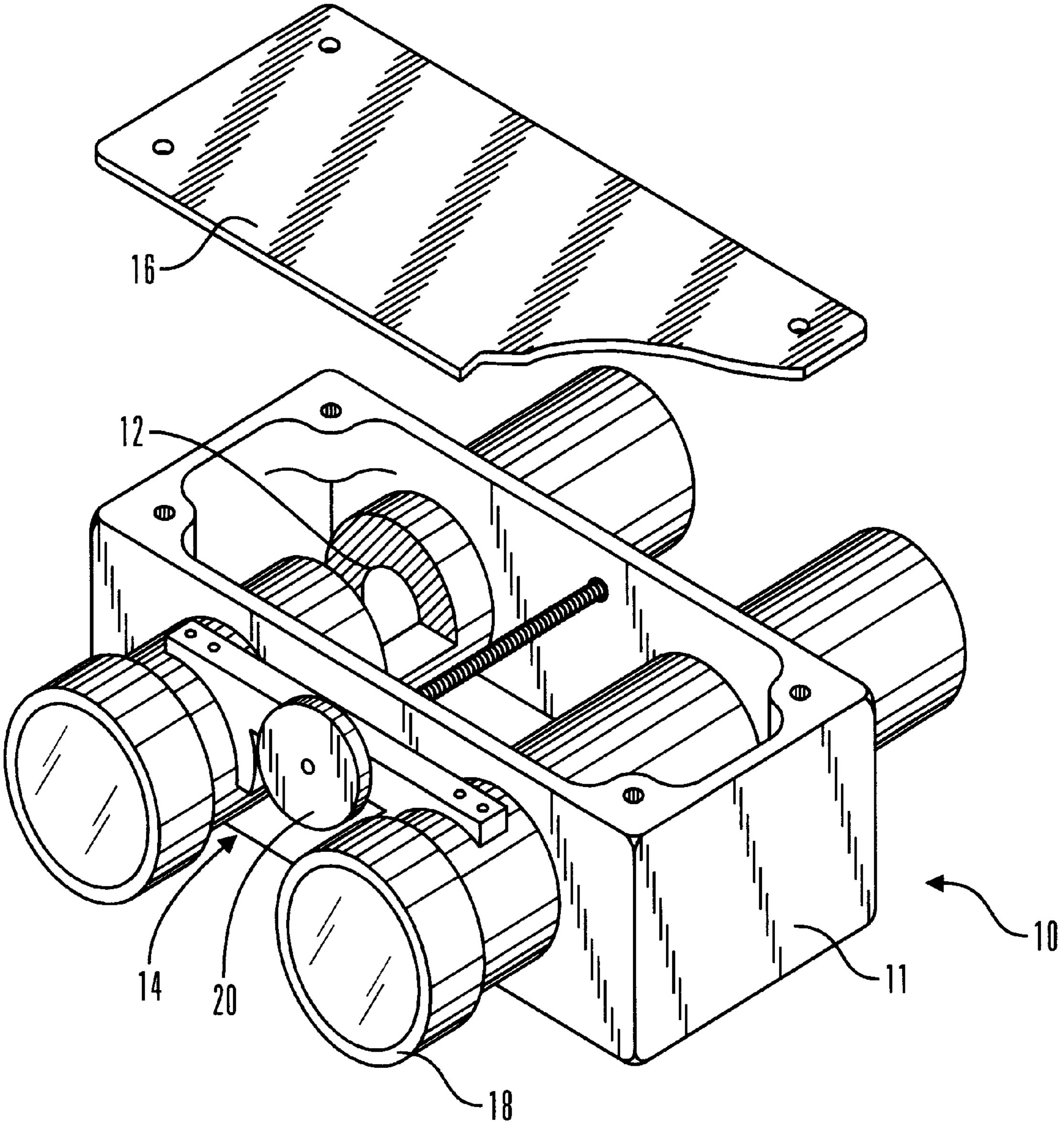
FIG. 1 is a schematic of the apparatus of the present invention.

The present invention is directed at an apparatus and method of using the apparatus for improving visual acuity of an individual in which the loss of acuity is the result of a "lazy" eye. The condition known as lazy eye can be overcome by exercising the eye according to the method of the invention.

Binoculars and high powered telescopes and lenses with large aperture or multiple focusing lenses and prisms in a binocular are used. Gradually the power of the lenses is increased to a focal length of a telescope and then to even extremely high-powered telescopes to provide vision clarity for an individual with uncorrectable vision. This use of multiple lenses and prisms in binoculars, in conjunction with focal lengths in a telescope, in gradual gradation of increase in power as well as high quality large apertures not only clear up fuzzy vision, reduces or eliminates low vision, lazy eyes (amblyopia) that are assumed to be uncorrectable; but also corrects different types of eye muscle disorders and weaknesses, as well as dyslexia, that are caused by irregular eye shifts and movements.

The apparatus comprises an opening for the insertion of lenses and prisms to provide sufficient power to the vision center in the brain that, with therapy sessions, corrects nearsightedness, farsightedness and direct and center crossed eyes or eyes that turn in and out by the virtue of visual feedback.

The binocular and telescopic devices in combination with large apertures also stimulate the optic nerves and tighten up the atrophied muscles to prevent facial deformity and speech impediment. Additionally, the incorporation of microscopes and magnifying glasses strengthen weak eye muscles. In general, the practice of the present invention corrects visual disorders that are not disease related.

In order to establish vision clarity one would have to determine the patient's focusing point or distance. (The distance or the point at which the candidate would see clearly.) Then the binoculars or a telescope are used to try to reach a point of clarity with a given degree of power depending on how near or far a candidate is from an object and also the size of the object.

Once the point an individual can see the clearest given an object at a distance is determined, then the power of the binoculars is increased or decreased for further clarity. At this point, one could determine the range at which the individual can see clearly. Then by using a telescope with a predetermined focal length, the range of clarity can be increased through infinity or by using a magnifying glass, or a microscope, smaller objects will be seen clearly.

This method incorporates a number of binoculars and telescopes for distance and several magnifying glasses for shorter distances. The apparatus of the present invention combines all of these devices into one single machine for making the necessary adjustments for distance and the size of the object to achieve clarity.

This machine provides different powered lenses and focal lengths along with large apertures in order to deliver clarity to a candidate with a lazy eye. Although it is complex to combine these three factors, namely power, large aperture, focal length, into a single instrument, a digitized computer would placate the task a great deal.

This instrument is suitable for use not only with lazy eyes, but also with other disorders, such as low vision and misaligned eyes and shifting or loose eyes in the socket. This not only stimulates the vision center in the brain, but also tightens up all the muscles from the vision center to the eyeball itself.

In trying to cure conditions such as "lazy eye" or "low vision" or dyslexia or irregular eye movements, the following treatments are necessary throughout the use of the instrument.

For instance, a candidate with a "lazy eye" would wear a patch on the good eye and look though a binocular instrument. The instrument 10 comprises a housing 11 with two openings 12 within the housing for insertion of a number of high-powered lenses and prisms and a means 14 for adjusting the focal length (shown in FIG. 1). A cover 16 is provided to close the instrument and eyepieces 18 for viewing an object through the instrument. An object of a certain size is placed at a distance in front of the observer. At this point, the instrument is adjusted with a knob 20 to move the high-powered lenses and prisms as well as increase or decrease the focal length so that the viewer sees the object perfectly clearly. This determines the focusing point for the weak eye. Then through a number of exercises, which include looking at different objects for the same distance and size of the object, the brain naturally makes an adaptation of seeing clearly with the weak eye—given this distance and size of the object. Once clarity is established at this focal point for the "lazy eye" through the use of this instrument, then the patch can be removed from the good eye in order to fuse two perfectly clear images, namely one from each eye, into one in the vision center of the brain. In doing so, the good eye of the amblyopic viewer is used as a guide to equal the resolution of the "lazy eye" with the good eye.

This process is repeated by moving the object away from its initial position for clarity of vision for far distances and closer to the viewer for clarity in near distances such as a reading distance -respectively. Of course, this would require a readjustment of the high-powered lenses, prisms and the focal length of the instrument. Through these exercises resolution or clarity for the "lazy eye" in every point in space—near or far is established. Once this is accomplished the candidate should recover from amblyopia because the vision in both eyes would be equal for any distance and any size object.

In the case of dyslexia, the viewer would look through the instrument with either one or both eyes open—depending on which eye is shifty and causes irregular movements of the eye within the socket. The high-powered lenses along with the focal length of the instrument, once again would strengthen the muscles around each eye as well as the fibers leading up to the vision center. By doing the exercises previously mentioned, the viewer's eye muscles should tighten up within the sockets therefore preventing the irregular movements of the images transposed into the vision center through the eyes and in the case of low vision these exercises would also be repeated. But instead of trying to establish vision clarity, the instrument with its high-powered lenses and focal length would stimulate the optic nerves and restore vision for the candidate. Again, the method of the exercise would depend on the eye or eyes affected.

EXAMPLE 1

Measurements were conducted on candidates with varying degrees of amblyopis—keeping in mind that each amblyopic case is unique to the individual. The measurements were taken with the necessary focal point adjustments.

The size of the "viewing image" was constant for all candidates at ⅜" (inch).

For reading and close-up viewing, 2×, 3×, 4× magnifying glasses were used. These powers are used for Patient No. 1 at 1 ft. or 2 ft. from the image for a perfect resolution (clarity).

Patient No. 1 at 20/25+ with a +0.75 amblyopia.

A. Resolution (clarity) at 5 ft. is reached with a pair of 3×35 binoculars.

B. Resolution (clarity) at 10 ft. is reached with a 4×30 binoculars.

C. Resolution at 20 ft. is reached with a 7×35 binoculars.

D. Resolution (clarity) at 30 ft. is reached with a 10×25 binoculars.

E. Resolution (clarity) at 40 ft. or 50 ft. is reached with a 10×50 binoculars.

F. Resolution (clarity) at 60 ft. and beyond is reached either with a higher-power binoculars or a telescope with the following specifications: 5×24 mm telescope; 60 mm objective lens, 800 mm focal length; w/a diagonal mirror and 3× lens/600 power. Note: The focal length has to be adjusted with distance.

EXAMPLE 2

Patient No. 2 at 20/30+ with a +1.00 amblyopia.

A. Resolution (clarity) at 5 ft. is reached with a pair of 3×35 binoculars.

B. Resolution (clarity) at 10 ft. is reached with a 4×30 binoculars.

C. Resolution (clarity) at 20 ft. is reached with a 7×35 binoculars.

D. Resolution (clarity) at 30 ft. is reached with a 10×25 binoculars.

E. Resolution (clarity) at 40 ft. or 50 ft. is reached with a 10×50 binoculars.

F. Resolution (clarity) at 60 ft. and beyond is reached either with a higher-power binoculars or a telescope with the following specifications: 5×24 mm telescope; 60 mm objective lens, 800 mm focal length; w/a diagonal mirror; and 3× lens/600 Power. Note: The focal length has to be adjusted with distance.

EXAMPLE 3

Patient No. 3 at 20/40 with a +1.50 amblyopia.

A. Resolution (clarity) at 5 ft. is reached with a pair of 3×35 binoculars.

B. Resolution (clarity) at 10 ft. is reached with a 4×30 binoculars.

C. Resolution (clarity) at 20 ft. is reached with a 7×35 binoculars.

D. Resolution (clarity) at 30 ft. is reached with a 10×25 binoculars.

E. Resolution (clarity) at 40 ft. or 50 ft. is reached with a 10×50 binoculars.

F. Resolution (clarity) at 60 ft. and beyond is reached either with a higher-power binoculars or a telescope with the following specifications: 5×24 telescope; 60 mm objective lens, 800 mm focal length; w/a diagonal mirror; and 3× lens/600 power. Note: The focal length has to be adjusted with distance.

EXAMPLE 4

Patient No. 4 at a range of 20/50 to 20/400 with a +2.00 amblyopia.

A. Resolution (clarity) at 5 ft. is reached with a pair of 4×30 binoculars due to a relatively higher prescription number.

B. Resolution (clarity) at 10 ft. is reached with a 7×35 binoculars.

C. Resolution (clarity) at 20 ft. is reached with a 10×25 binoculars.

D. Resolution (clarity) at 30 ft. is reached with a 10×50 binoculars.

E. Resolution (clarity) at 40 ft. or 50 ft. is reached with also a 10×50 binoculars.

F. Resolution (clarity) at 60 ft. and beyond is reached either with a higher-power binoculars or a telescope with the following specifications: 5×24 mm telescope; 60 mm objective lens, 800 mm focal length; w/a diagonal mirror; 3× lens/600 Power. Note: The focal length and the eye piece have to be adjusted with distance.

In the previous examples of Patient Nos. 1, 2, 3 & 4, as the amblyopic condition gets worse or as the prescription of the lenses gets higher and higher for the same given distances; the Power of the binoculars has to increase to a point that we use telescopes to reach "The Clarity" relative to the distance. Of course, the focal point and the focal length have to be adjusted for any given point in space between the "viewing image" and the "Observer's Eye".

EXAMPLE 5 amblyopia cases have also been tested with different viewing ranges and severely high prescriptions. The results were as follows.

Patient Nos. 5, 6 & 7 with prescriptions of +3.00, +4.00 & +5.00 respectively.

A. Resolution (clarity) for candidates 5, 6 & 7 at 5 ft. from the "viewing image" was reached with a pair of 10×25 binoculars.

B. Resolution (clarity) at 10 ft. from the "viewing image" for all three candidates was also reached with a 10×25 binoculars.

C. Resolution (clarity) at 20 ft. for all three candidates was reached with a 10×50 binoculars.

D. Resolutions (clarity) at 30 ft. and beyond for all three candidates was reached with the specified telescope with a different eye piece per given distance. For example, 5×24 telescope; 60 mm objective lens, 800 mm focal length; w/a diagonal mirror; 3× lens/600 power.

Through this process of providing clarity or (resolution) for every point in space between the observer and the "viewing image", the amblyopic candidate should program each image clearly into the vision center in the brain. By the virtue of natural adaptation and constant feedback of perfectly clear images, the light will be focused at the dead center of the retina or namely the fovea.

In short, as mentioned in my specific theories, an instrument that would combine all these devices into one will produce the desired results and should eliminate amblyopia of any degree.

Another effect that was observed through these preliminary tests was that both certain types of dyslexia and "low vision" that were associated with "lazy eyes" had been substantially reduced.

This process of "power feedback" rejuvenates all muscles around the eye, the fibers from the optic nerves leading to the vision center as well as the crystalline lens of the eye. Therefore reducing or eliminating certain dyslexia and "low vision".

The above specification, examples and data provide a complete description of the manufacture and use of the composition of the invention. Since many embodiments of the invention can be made without departing from the spirit and scope of the invention, the invention resides in the claims hereinafter appended.

What is claimed is:

1. A method for treating muscular disorders of the eye comprising:

a. placing an object in front of the patient at a predetermined distance;

b. placing a binocular optical system comprising lenses and prisms between the objects and the patient's eyes;

c. placing a patch over the patient's strong eye;

d. adjusting the focal length of the optical system so that the objects are clearly resolved by the patient;

e. removing the patch from the good eye so that the patient can repeat the exercise described in step d. using both eyes;

f. repeating steps c. through e. after placing the object at a greater distance from the patient; and g. repeating step f. until the resolution observed with the patient's weak eye is equal to the resolution observed with the patient's strong eye.

2. The method as recited in claim 1 wherein the optical system includes high powered lenses and prisms.

3. A device for the treating muscular disorders of the eye comprising:

a housing;

eyepieces attached to a first side of the housing;

an optical system comprising movable lenses and prisms;

two openings within the housing for receiving the lenses and prisms such that the lenses and prisms are in alignment with the eye pieces;

means for adjusting the focal length of the device:

means for moving the lenses and prisms so that an object viewed by a patient through the eye pieces, lenses and prisms is clear and resolved; and a cover for enclosing the openings.

* * * * *